US008454648B1

(12) United States Patent
Isham (10) Patent No.: US 8,454,648 B1
(45) Date of Patent: Jun. 4, 2013

(54) LOCKING DEVICE FOR A PROSTATE IMMOBILIZER

(75) Inventor: John Isham, Houston, TX (US)

(73) Assignee: RadiaDyne LLC, Houston, TX (US)

( * ) Notice: Subject to any disclaimer, the term of this patent is extended or adjusted under 35 U.S.C. 154(b) by 323 days.

(21) Appl. No.: 12/410,639

(22) Filed: Mar. 25, 2009

(51) Int. Cl.
*A61M 29/00* (2006.01)

(52) U.S. Cl.
USPC ............ 606/197; 604/96.01; 604/101.05; 604/509; 604/513; 600/427; 606/192; 128/DIG. 26

(58) Field of Classification Search
USPC ............ 606/191–199; 604/96.01, 103.03, 604/100.01, 100.02, 117, 101.05, 180, 192; 24/30.5 R, 132 A, 132 AA, 132 WL; 43/17, 43/43.1, 43.11, 43.12, 43.13, 43.14, 43.15; 128/DIG. 26
See application file for complete search history.

(56) References Cited

U.S. PATENT DOCUMENTS

| | | | | |
|---|---|---|---|---|
| 4,291,698 | A | * | 9/1981 | Fuchs et al. ............... 606/232 |
| 4,584,730 | A | | 4/1986 | Rajan |
| 4,893,367 | A | | 1/1990 | Heimreid et al. |
| 5,203,774 | A | * | 4/1993 | Gilson et al. ............ 604/165.01 |
| 5,476,095 | A | | 12/1995 | Schnall et al. |
| 5,486,193 | A | * | 1/1996 | Bourne et al. ............... 606/194 |
| 5,522,103 | A | | 6/1996 | Kier et al. |
| 5,832,550 | A | | 11/1998 | Hauger et al. |
| 5,836,306 | A | * | 11/1998 | Duane et al. ............... 600/585 |
| 6,106,487 | A | * | 8/2000 | Duane et al. ............... 600/585 |
| 6,113,062 | A | * | 9/2000 | Schnell et al. ............... 251/10 |
| 6,327,724 | B1 | | 12/2001 | Sharrock et al. |
| 7,216,385 | B2 | | 5/2007 | Hill |
| 2003/0028097 | A1 | * | 2/2003 | D'Amico et al. ............ 600/427 |
| 2007/0276332 | A1 | * | 11/2007 | Bierman ..................... 604/174 |
| 2008/0034640 | A1 | * | 2/2008 | Naerheim et al. ........... 43/44.92 |

OTHER PUBLICATIONS

U.S. Appl. No. 10/211,480, filed Aur. 2, 2002, D'Amico et al.
U.S. Appl. No. 11/623,702, filed Jan. 16, 2007, Isham.
U.S. Appl. No. 11/933,018, filed Oct. 31, 2007, Isham.
U.S. Appl. No. 11/966,544, filed Dec. 28, 2008, Isham.
D'Amico, Anthony V. et al., "A Practical Method to Achieve Prostate Gland Immobilization and Target Verification for Daily Treatment," Int. J. Radiation Oncology Biol. Phys., 2001 pp. 1431-1436. vol. 51 No. 5, ©2001 Elsevier Science Inc., U.S.A. (6 pages).
D'Amico, Anthony V. at al., "A Prospective Evaluation of Rectal Bleeding After Dose-Escalated Three-Dimensiona Conformal Radiation Therapy Using an Intrarectal Balloon for Prostate Gland Localization and Immobilization," 2005, Journal Urology, pp. 780-784, vol. 67, No. 4, 02006 Elsevier Inc. (5 pages).

(Continued)

*Primary Examiner* — Gary Jackson
*Assistant Examiner* — Katrina Stransky
(74) *Attorney, Agent, or Firm* — Boulware & Valoir (57) ABSTRACT

A prostate immobilizer has a shaft with a fluid passageway extending therethrough, a balloon affixed over an end of the shaft such that the fluid passageway communicates with an interior of the balloon, a lumen extending within the shaft so as to have an end opening adjacent an end of the balloon, and a device for locking a position of the shaft. The device has a positioning member having a stem portion extending from a head portion, and a locking member having a locked position and an unlocked position. The locking member cooperates with the stem portion of the positioning member so as to fix a position on the shaft. A channel is formed in the head portion so as to receive the shaft therein.

19 Claims, 4 Drawing Sheets

OTHER PUBLICATIONS

Little, Darren J. et al., "Use of Portal Images and BAT Ultrasonography to Measure Setup Error and Organ Motion for Prostate IMRT: Implications for Treatment Margins," Intl J. Radiation Oncology Biol. Phys., 2003, pp. 1218-1 224, vol. 56, No. 5 © 2003 Elsevier Inc, (7 pages).

McGary, John E. et al., "Prostate Immobilization Using a Rectal Balloon," Journal of Applied Clinical Medical Physics, 2002, pp. 6-11, vol. 3, No. 1, © 2002 Am. Coll. Med. Phys. (6 pages).

Patel, Rakesh R. et al., "Rectal Dose Sparing with a Balloon Catheter and Ultrasound Localization in Conformal Radiation Therapy for Prostate Cancer," Radiotherapy & Oncology Journal of the European Society for Therapeutic Radiology and Oncology, 2003, pp. 285-294, vol. 67, © 2003 Elsevier Science Ireland Ltd. (10 pages).

Van Lin, Emile N. J. TH. et al., "Rectal Wall Sparing Effect of Three Different Endorectal Balloons in 3D Conformal and IMRT Prostate Radiotherapy," Int'l J. Radiation Oncology Biol. Phys., 2005, pp. 565-576, vol. 63, No. 2 © 2005 Elsevier, Inc. (12 pages).

Poli, M. Esmeralda Ramos et al., "An Assessment of PTV Margin Definitions for Patients Undergoing Conformal 3D External Beam Radiation Therapy for Prostate Cancer Based on an Analysis of 10,327 Pretreatment Daily Ultrasound Localizations," Int. J. Radiation Oncology Biol. Phys., 2007, pp. 1430-1437, vol. 67, No. 5, © Elsevier Inc. (8 pages).

Pollack, Alan et al., "Prostate Cancer Radiation Dose Response: Results of the M.D. Anderson Phase III Randomized Trial," Int. J. of Radiation Oncology Biol. Phys., 2002, pp. 1097-1105, vol. 53, No. 5, © 2002 Elsevier Science Inc. (9 pages).

Storey, Mark R. et al., "Complications from Radiotherapy Dose Escalation in Prostate Cancer: Preliminary Results of a Randomized Trial," Int J. Radiation Oncology Biol. Phys., 2000, pp. 635-642, vol. 48, No. 3, © 2000 Elsevier Science Inc. (8 pages).

Van Lin, Emile N.J. TH. et al., "Reduced Late Rectal Mucosal Changes After Prostate Three-Dimensional Conformal Radiotherapy with Endorectal Balloon as Observed in Repeated Endoscopy," Int. J. Radiation Oncology Biol. Phys., 2007, pp. 799-811, vol. 67, No. 3, © 2007 Elsevier Inc. (13 pages).

Wang. Zhou et al., "The Effect of Positional Realignment on Dose Delivery to the Prostate and Organs-at-Risk for 3DCRT," Medical Dosimetry, 2007, pp. 1-6, vol. 32, No. 1, © 2007 American Association of Medical Dosimetry (6 pages).

Zietman, A. L. et al., "A Randomized Trial Comparing Conventional Dose (70.2 GyE) and High-Dose (79.2 GyE) Conformal Radiation in Early Stage Adenocarcinoma of the Prostate: Results of an Interim Analysis of RROG 45-09," Int. J. Radiation Oncology Biol. Phys., 2004, pp. S131-S132, vol. 60, No. 1, Supp. 2004, © 2004 Elsevier B. V. (2 pages).

* cited by examiner

LOCKING DEVICE FOR A PROSTATE IMMOBILIZER

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to an apparatus for diagnosing and therapeutically treating disease. Particularly, the present invention relates to prostate immobilization and isolation during radiation treatment of prostate cancer. More particularly, the present invention relates to an apparatus that calibrated the position of a rectal balloon for repeated radiation treatment of a prostate. The present invention also relates to devices for repeatedly immobilizing the prostate.

2. Description of Related Art Including Information Disclosed Under 37 CFR 1.97 and 37 CFR 1.98.

Treatment of prostate cancer using radiation therapy is difficult due to the prostate's position near radiation-sensitive tissues. Treatment is further complicated by prostate motion. Adenocarcinoma of the prostate commonly occurs in the posterior portion of the prostate gland which is in very close proximity to the rectal wall. To plan external beam radiation treatment, urethrograms, CT scans and magnetic resonance imaging (MRI) have all been used to visually localize the prostate, as well as the normal critical structures in the surrounding area.

Typically, the planning of radiation therapy for the treatment of prostate cancer involves the patient undergoing a CT-based simulation scan of the pelvis to determine the location of the prostate gland. In the simulation phase, the patient is placed on CT equipment that is preferably similar to the radiation treatment equipment (except that it does not generate the high, energy radiation beam). The simulation equipment is positioned to simulate the delivery of the sequence of treatment beams prescribed by the treating oncologist. Normally, during the simulation procedure, CT images are acquired. CT images allow the oncologist to locate the position of the tumor and help to facilitate the composition of a radiation treatment plan. The treatment plan delineates the positions of the radiation equipment components for delivery of the treatment beams.

During the actual treatment phase, the patient is placed in the same position on the treatment equipment as in the simulation scans. Radiation-emitting devices are generally known and are used for radiation therapy in the treatment of patients. Typically, a radiation therapy device includes a gantry, which can be swiveled around a horizontal axis of rotation in the course of a therapeutic treatment. A linear accelerator is located in the gantry for generating a high-energy radiation beam. During treatment, the radiation beam is provided by this equipment and is delivered to the patient at the precise location as delineated by the physician during simulation. A further feature of radiation therapy involves portal images, which are commonly used in radiation therapy to verify and record the patient tumor location. Portal images include manual (film) and electronic images (EPI) taken before and/or after the treatment.

During external beam radiation therapy, radiation is directed to the target prostate which is near the rectal wall. A misdirected radiation beam may perforate the rectal wall causing radiation proctitis (rectal bleeding). This toxicity is related to the total radiation dose prescribed and the volume of the anterior rectal wall receiving a high radiation dose. A major factor limiting radiation oncologists' attempts to reduce the volume of the anterior rectal wall receiving a high radiation dose is the position of the prostate gland as well as the intrinsic motion up to 5 millimeters in the anterior to posterior direction caused by rectal peristalsis. Accordingly, oncologists generally will add a margin to the radiation field in order to ensure that the entire prostate gland receives the prescription dose. This margin is typically on the order of 5 to 15 millimeters. As a consequence, lower doses of radiation may need to be used so as not to overexpose radiation sensitive structures. However, this may lead to inadequate radiation treatment and a higher probability of local cancer recurrence.

Various patents and patent publications have issued relating to apparatus for radiation treatment of the prostate. For example, U.S. Pat. No. 5,476,095, issued on Dec. 19, 1995 to Schnall et al., discloses an insertable pickup probe for use in providing diagnostic MRI images. The preferred embodiment is used in imaging the prostate and has an elongated shaft supporting an inflatable patient interface balloon at its distal end. The interface balloon has an inner balloon and an outer balloon, between which a receiving coil is positioned. A lumen for air supply is provided in the shaft for expanding the inner balloon against the outer balloon to place the receiving coil in close proximity to the area of interest in order to provide MRI images.

U.S. patent application Ser. No. 10/211,480, filed on Aug. 2, 2002 to D'Amico et al., discloses an immobilizer probe system and method. This system has an insertable probe for immobilizing a region of interest during staging and radiation therapy thereof. In particular, this device uses a balloon having a rectangular cross section connected to a shaft. The shaft extends to an end of the balloon so as to allow fluid flow through an interior of the shaft and into the balloon so as to selectively inflate the balloon once the balloon is installed into the rectal cavity. The balloon, shaft, and handle are bonded together so that they move radially as a single unit when torque is applied. A syringe is provided which connects the shaft and serves as an air pump to deliver a volume-limited amount of air to the air lumen of the shaft to the balloon. A stop cock is provided to maintain the air within the balloon.

U.S. application Ser. No. 11/623,702, filed on Jan. 16, 2007 by the present inventor, discloses a rectal balloon apparatus that has a shaft with a fluid passageway extending therethrough, a balloon affixed over an end of the shaft such that the fluid passageway communicates with the interior of the balloon, and a sleeve slidably affixed over the shaft. This sleeve is movable between a first position overlying the balloon and a second position away from the balloon. The sleeve has an aperture at an end thereof such that the balloon extends outwardly of this aperture.

U.S. application Ser. No. 11/933,018, filed on Oct. 31, 2997 by the present inventor, is a continuation-in-part of U.S. application Ser. No. 11/623,702. This application additionally describes the balloon as having a laterally flat surface thereon when inflated. There is a longitudinal groove extending along the laterally flat surface. Together, the laterally flat surface and the groove enhance the seating of the prostate on the balloon. Additionally, the application describes a valve assembly on the end of the shaft opposite the balloon. A fluid introducing means is removably attached to the valve assembly to introduce fluid into the valve assembly and move the balloon from the non-inflated condition to the inflated condition.

U.S. patent application Ser. No. 11/966,544, filed on Dec. 28, 2008 by the present inventor, discloses a rectal balloon apparatus has a shaft with a fluid passageway extending therethrough. A balloon is affixed over an end of the shaft such that the fluid passageway communicates with an interior of the balloon. A lumen extends along the shaft so as to allow bodily gas pressure to pass therethrough. The balloon has a laterally flat surface thereon when inflated. A sleeve is positioned over a portion of the shaft. The lumen is affixed to a surface of the sleeve. The sleeve has a first portion and a second portion frangibly connected together.

A problem associated with the use of prostate immobilizers, i.e. rectal balloon apparatus, is that the immobilizers must be repeatedly positioned near the prostate over the course of many treatments. Insertion techniques can vary greatly between treatments. This can cause a change in the depth of the inserted balloon. The patient can often squeeze the sphincter muscles during insertion and treatment. This can also change the position of the balloon. This can result in different positionings of the balloon, and a variation of the immobilized prostate's position, and the tissues surrounding the prostate, such that radiation treatment from session to session is not as exact as it should be. Thus, there is a need for a device that can repeatably position a prostate immobilizer for accurate radiation treatment of a prostate over multiple sessions.

Another problem associated with prostate immobilizers is that the positioning of the immobilizer can be a matter of guesswork by the hospital personnel involved. Thus, there is a need for more precise positioning of the prostate immobilizers.

U.S. patent Ser. No. 12/141,270, filed on Jun. 18, 2008 by Isham, discloses a rectal balloon apparatus has a shaft with a fluid passageway extending therethrough. A balloon is affixed over an end of the shaft such that the fluid passageway communicates with an interior of the balloon. The balloon has a laterally flat surface thereon when inflated. The laterally flat surface of the balloon has a longitudinal groove formed thereon. The balloon has a radiation sensor positioned within the groove and a plurality of fiducial markers positioned on a surface of the balloon. A stopper is slidably mounted on the shaft. When it is desired to measure the radiation dose by the radiation sensor, it is imperative that the accurate positioning be achieved. The radiation sensor achieves maximum accuracy and effectiveness when it positioned accurately in the same position during radiation treatment.

It is an object of the present invention to provide a device for a prostate immobilizer whereby the position of the balloon can be easily ascertained by medical personnel.

It is another object of the present invention to provide a device for a prostate immobilizer that allows medical personnel to re-position the apparatus in substantially the same orientation in successive treatment sessions.

It is another object of the present invention to provide a device for a prostate immobilizer that is easy to use and easy to install.

It is another object of the present invention to provide a prostate immobilizer which maximizes the comfort of the patient.

It is another object of the present invention to provide a prostate immobilizer which enhances the ability to properly seat the prostate on a flat surface of the rectal balloon.

It is another object of the present invention to provide a prostate immobilizer which avoids potential allergic reactions.

It is still another object of the present invention to provide a prostate immobilizer which is easy to manufacture and relatively inexpensive.

It is still another object of the present invention to provide a prostate immobilizer which has improved holding stability when inflated.

These and other objects and advantages of the present invention will become apparent from a reading of the attached specification and appended claims.

BRIEF SUMMARY OF THE INVENTION

The present invention is a locking device for use on a shaft of a prostate immobilizer. The locking device has a positioning member with a head portion and a stem portion. The locking member extends over the stem portion. The stem portion extends from the head portion. The stem portion has a channel formed therein. This channel is suitable for receiving the shaft of the prostate immobilizer therein. The locking member is movable between a locked position and an unlocked position. The locking member has a surface suitable for gripping the shaft when the locking member is in the locked position.

In the present invention, the locking member is hingedly connected to the stem portion. The stem portion has a lip formed thereon. The locking member has a latch formed thereon. The latch engages the lip when the locking member is in the locked position. The channel extends through the stem portion and the head portion. The channel has a plurality of ribs formed on an inner wall thereof. This plurality of ribs compressively engaging the shaft when the locking member is in the locked position.

The stem portion has an outer surface that is flush with a surface of the head portion. The locking member has an outer surface flush with another surface of the head portion when in the locked position. The head portion has a generally hemispherical shape at one end thereof. The head portion has a generally flat surface at an opposite end thereof. The locking member is positioned adjacent the generally flat surface. The head portion has a longitudinal split formed therein so as to open to the channel. This longitudinal split has an opening suitable for allowing the shaft to pass therethrough and into the channel.

DETAILED DESCRIPTION OF THE INVENTION

Figure 1:
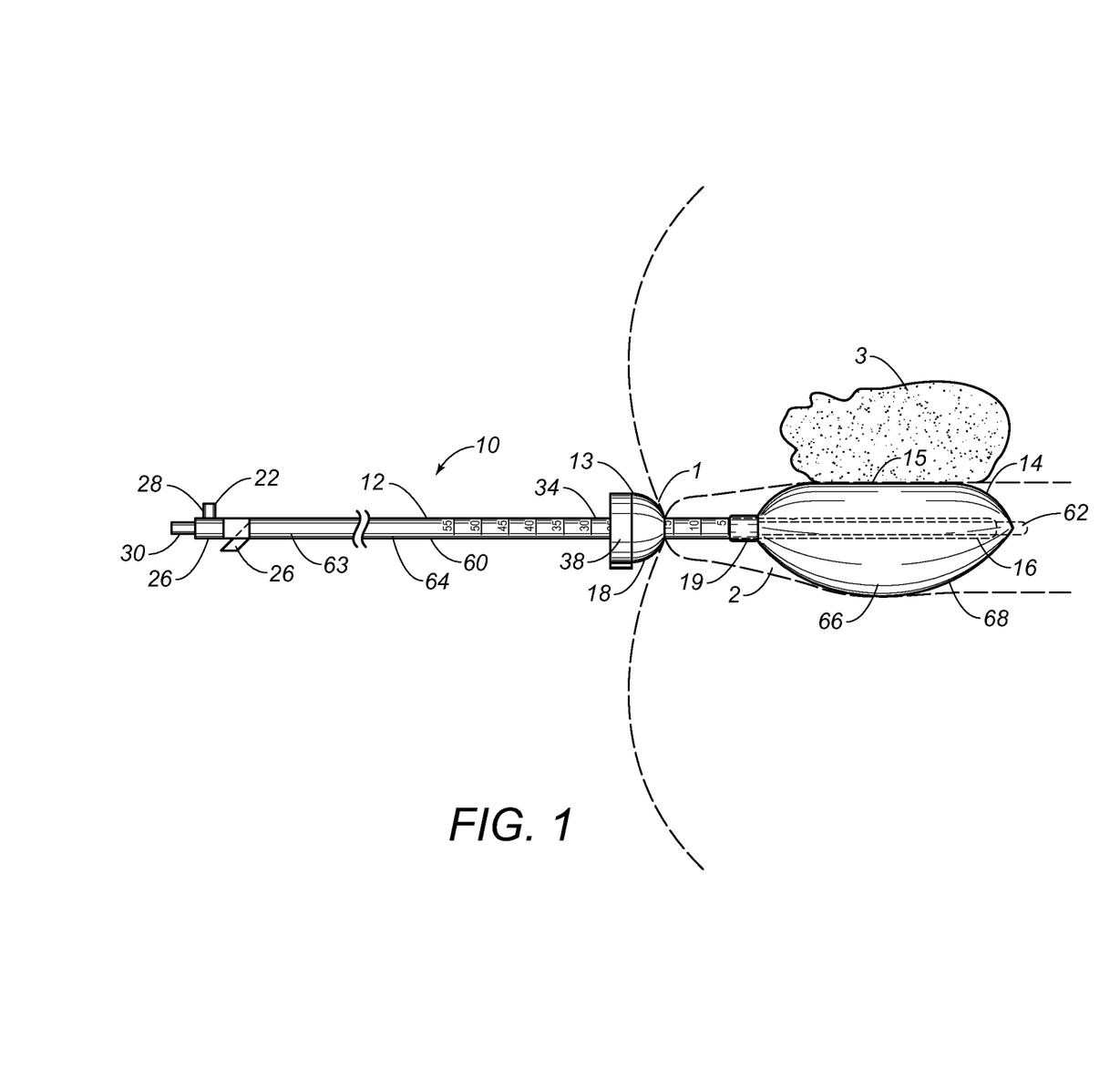
FIG. 1 shows a diagrammatic illustration of the preferred embodiment of the prostate immobilizer of the present invention as applied within the anal canal.

Referring to FIG. 1, there is shown a side elevational view of the preferred embodiment of the prostate immobilizer 10 of the present invention. The prostate immobilizer 10 has a shaft 12 having a fluid passageway 64 extending therethrough, a balloon 14 extending over an end 16 of the shaft 12 such that the fluid passageway 64 communicates with an interior 66 of the balloon 14, a lumen 60 extending within the shaft 12 so as have an end 62 opening adjacent an end 68 of the balloon 14, and a locking device 13 for locking a position of the shaft 12 of the prostate immobilizer 10. The device 13 adjustably slidable along the shaft 12. The device 13 serves to assure uniformity in the positioning of the balloon 14 in the rectal cavity 2 adjacent the prostate 3 during radiation therapy.

The shaft 12 is a generally longitudinal shaft with the fluid passageway 64 extending through a center thereof. The shaft 12 is made of a flexible material. A valve assembly 22 is affixed to an end of the shaft 12 opposite the balloon 14. The valve assembly 22 can have a variety of configurations. FIG. 1 illustrates the valve assembly 22 as an inline valve assembly configuration. The valve assembly 22 may also be an angled valve assembly configuration. The valve assembly 22 includes a stopcock 26. A valve 28 facilitates the ability of the stopcock 26 to open and close so as to selectively allow the fluid to pass into the shaft 12. A port 30 allows the valve assembly 22 to be connected to a supply of the fluid. When the stopcock 26 is opened by the rotation of the valve 28, the fluid will flow through the valve assembly 22, through the fluid passageway 64 of the shaft 12 and into the interior 66 of the balloon 14. The valve 28 can then be closed so as to maintain the inflated configuration of the balloon 14. When the procedure is finished and the fluid needs to be removed from the balloon 14, the valve 28 of stopcock 26 can then be opened so as to allow for the release of fluid therethrough.

The end 16 of the shaft 12 is adjacent the end 68 of the balloon 14. The end 16 of the shaft 12 is suitably curved or domed-shaped so as to allow the shaft 12 to facilitate the introduction of the balloon 14 into the rectal cavity 2. The prostate immobilizer 10 is inserted into the rectal cavity 2 through rectum 1. The shaft 12 has indicia 34 formed therealong. The indicia 34 has numerical references associated therewith. The numerical references are indicative of the distance that the balloon 14 is inserted into the rectum 1. The indicia 34 provide a clear indication to medical personnel of the position of the balloon 14 in the rectal cavity 2. The balloon 14 can be removed and re-inserted into the rectal cavity 2. The device 13 is affixed to the shaft 12 so that the balloon 14 will be repositioned for a same distance into the rectal cavity 2 adjacent the prostate 3.

In FIG. 1, the locking device 13 is shown as positioned where indicia 34 number "15". A ring 19 is affixed to the shaft 12 adjacent the balloon 14. The ring 19 has a color different than a color of the shaft 12 so that the ring 19 can be seen by medical personnel. For example, the ring 19 can be of a bright color, such as blue or radioluminescent, so as to provide the medical personnel with positive indication when the balloon 14 is past the anal verge. The ring 19 can also displace the anal verge so as to enhance comfort during removal of the balloon 14. The ring 19 is approximately five millimeters in length. The ring 19 has a diameter greater than a diameter of the shaft 12. This makes it easier to remove the balloon 14 (the widening of the anal verge keeps it from closing up after the balloon 14 is inserted.

The device 13 is positioned on the shaft 12. Once the balloon 14 is positioned in a desired location adjacent the prostate 3, medical personnel position the device 13 so that it is adjacent the rectum 1 and holds the prostate immobilizer 10 in position. The balloon 14 is shown as in inflated condition. The lumen 60 extends within the shaft 12 so as to have an end 62 opening adjacent an end 68 of the balloon 14. A fluid is introduced through the valve assembly 22 and through the fluid passageway 64 of the shaft 12 so as inflate the balloon 14. The balloon 14 has seating area 15, which a flat portion of the outer surface of the balloon 14. The seating area 15 is positioned adjacent the prostate 3 when in the rectal cavity 2. To change the balloon from the inflated condition to the deflated condition, the valve assembly 22 can be opened so as to allow fluid to move from the interior 66 of the balloon 14, through the fluid passageway 64 and the shaft 12, and out of the valve assembly 22. The prostate immobilizer 10 is inserted and removed from the rectum 1 in the deflated condition. The lateral flatness of the seating area 15 prevents the prostate 3 from sliding laterally. The rounded outer surface of the balloon 14 generally contacts the wall of the rectal cavity 2. The balloon 14 can be formed of a non-latex material so as to avoid allergic reactions.

Referring still to FIG. 1, the lumen 60 for the prostate immobilizer 10 extends within the fluid passageway 64 of the shaft 12. The lumen 60, although shown on the interior of the shaft 12 in FIG. 1, can be in any other orientation, such as on the outer surface of the shaft 12, that allows for a second fluid passageway in the prostate immobilizer 10. In FIG. 1, the lumen 60 has end 62 that extends out the balloon 14. End 62 of the lumen 60 has opening that allows for bodily gases to escape from the rectal cavity 2 and out of the lumen 60. A one-way valve can be included along the length of the lumen 60 so as to only allow fluids to pass from the rectal cavity 2 to the outside environment through the lumen 60. Holes can be formed in the outer surface of the shaft 12 in the portion of the shaft 12 that extends within the interior 66 of the balloon 14 so as to allow fluids to pass into and out of the interior 66 of the balloon 14.

During subsequent radiation treatments, the locking device 13 can be affixed to the shaft 12 in the same position as shown in FIG. 1. As such, when the balloon 14 is inserted, the shaft 12 can be urged forward until the locking device 13 contacts the entrance of the rectal cavity 2. As such, the medical personnel are assured that the balloon 14 is in the proper position. This is accomplished accurately regardless of any change of medical personnel, any squeezing of the sphincter muscles by the patient, and any variations in the amount of lubrication jelly that is used. As such, repeatability is assured. Repeatability is particularly important when radiation sensors are used in conjunction with the balloon. When the locking device is affixed to the shaft, it will not be easily displaced, even if excess lubrication resides on the shaft. The smooth contour of the outer surface provides comfort to the patient.

Figure 2:
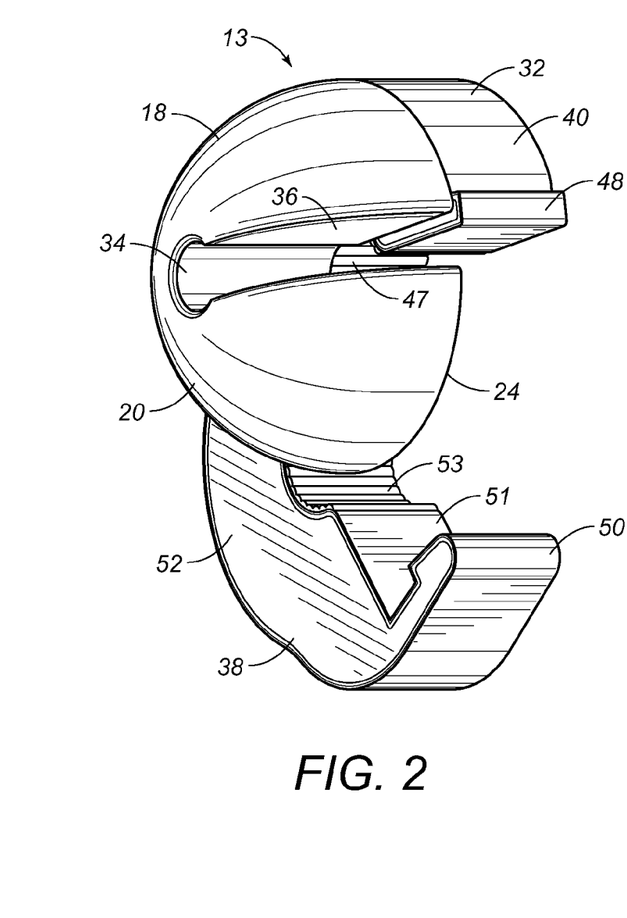
FIG. 2 shows a perspective view of the preferred embodiment of the locking device of the present invention as shown in an unlocked position.

Referring to FIG. 2, there is shown a perspective view of the preferred embodiment of the device 13 for locking in a position onto the shaft 12 of a prostate immobilizer 10 of the present invention. The locking device 13 is illustrated in an unlocked position prior to attaching to the shaft 12. The device 13 has a positioning member 18 and a locking member 38. The positioning 4 member 18 has a head portion 20 and a stem portion 32. The stem portion 32 is integrally formed adjacent an end 24 of the head portion 20. The positioning member 18 has a channel 34 formed therein. The channel 34 extends through each of the head portion 20 and the stem portion 32. The positioning member 18 has a longitudinal split 36 formed therein. The longitudinal split 36 extends through the head portion 20. The longitudinal split 36 communicates with the channel 34. The locking member 38 has a locked position and an unlocked position. The locking member 38 is hingedly connected to the portion, 32 of the positioning member 18. The head portion 20 of the positioning member 18 has a hemispherical shape. The stem portion 32 of the positioning member 18 has an outer surface flush with an outer surface of the head portion 20. The longitudinal split 36 extends for the entire length of the head portion 20. The longitudinal split 36 has a width slightly greater than the diameter of the shaft 12. This allows the shaft 12 to be introduced into the cannel 34.

The stem portion 32 has an outer surface 40 that is flush with an outer surface of the head portion 20. As such, the locking device 13 has smooth contours on the outer surface thereof. The stem portion 32 has a lip 48 extending and angling upwardly and outwardly of the outer surface 40. The lip 48 is generally adjacent to the wall of the longitudinal split 36 of the head portion 20. A curved surface 47 is formed on the interior of the stem portion 32 and has a plurality of ribs formed thereon. The curved surface 47 devices a portion of the channel 34. The longitudinally-extending ribs on the curved surface 47 of channel 34 provide a structure that can suitably grip the outer surface of the shaft so as to facilitate the ability to fix the position of the locking device 13 on shaft 12.

The locking member 38 is hingedly connected to the stem portion 32. The locking member 50 includes a latch 50 that has an edge that will engage the lip 48 of the stem portion 32. The inner surface 51 of the locking member 50 includes a curved area 53. Curved area 53 generally corresponds with the location of the curved surface 47 of stem portion 32. As such, curved area 53 will cooperate with the curved surface 47 so as to define the channel 34 of the positioning member 18 when the locking member 38 is in a locked position. The locking member 38 also has an inner surface 52 which will reside in proximity with the end 24 of the head portion 20.

Figure 3:
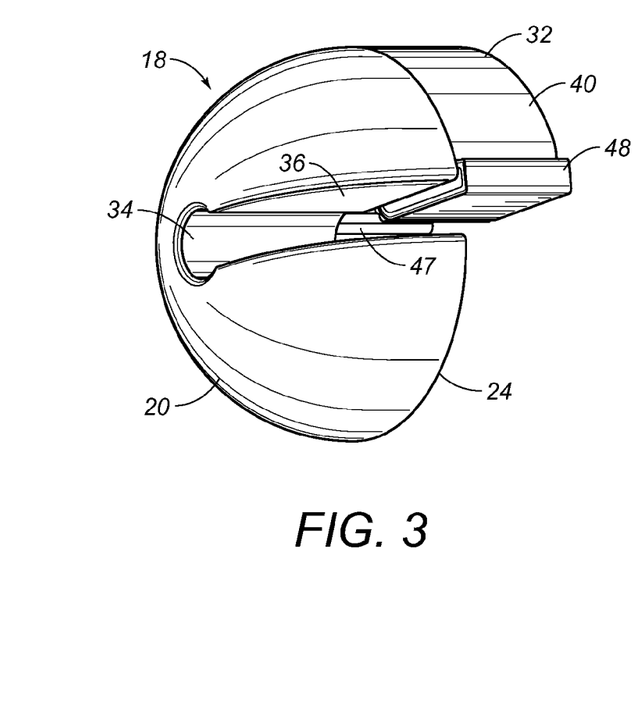
FIG. 3 shows an isolated perspective view of the positioning member of the locking device of the present invention.

Referring to FIG. 3, there is shown an isolated perspective view of the positioning member 18 of the present invention. The head portion 20 is hemispherical in shape. The channel 34 is formed generally centrally of the head portion 20. The stem portion 32 extends from the end 24 of the head portion 20. The longitudinal split 36 is formed in the head portion 20 and the stem portion 32 so that the shaft 12 of the prostate immobilizer 10 can be inserted through the longitudinal split 36 so as to reside in the channel 34. The channel 34 thus has an inner diameter that is suitable for receiving the shaft 12. The longitudinal split 36 thus has a width that is suitable for passing the shaft 12 therethrough into and out of the channel 34. The hemispherical shape of the head portion 20 is comfortable when positioned against the rectum 1, the head portion 20 has contours that match the contours of the rectum 1.

The stem portion 32 is illustrated as having the lip 48 extending angularly outwardly from the outer surface 40 thereof. The curved surface 47 is formed on the interior of the stem portion 32 in alignment with the channel 34 of the head portion 20.

Figure 4:
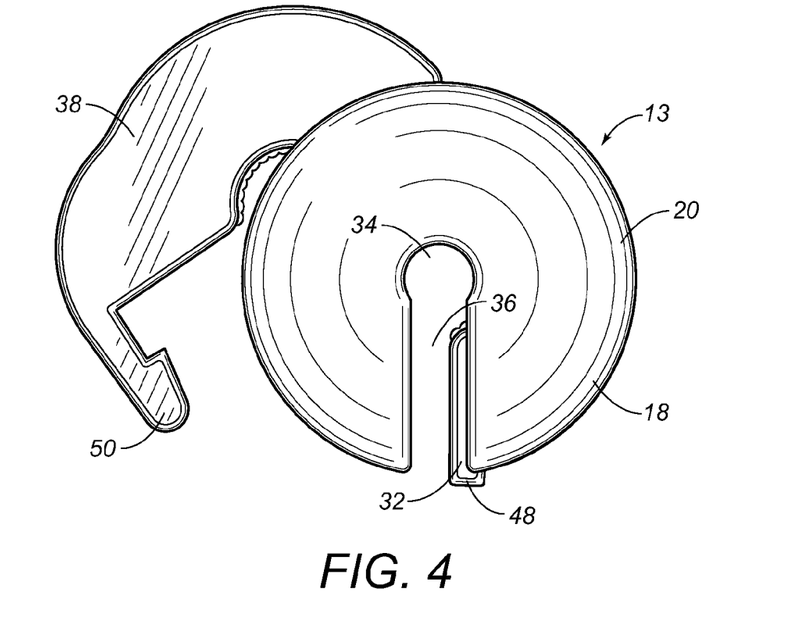
FIG. 4 shows an end view of the preferred embodiment of the locking device of the present invention in an unlocked position.

Referring to FIG. 4, there is shown an end perspective view of the device 13 of the present invention. The device 13 can be called a stopper or locking stopper. The locking member 38 is shown in the unlocked position. Thus, the latch 50 is spaced from the lop 48 of the stem section 32. The contour of the outer wall of the locking member 38 generally matches the contour of the outer surface of the positioning member 18. The channel 34 can be seen extending for the entire of the head portion 20 and the stem portion 32. The shaft 12 of the prostate immobilizer 10 is inserted through longitudinal split 36 and into the channel 34.

Figure 5:
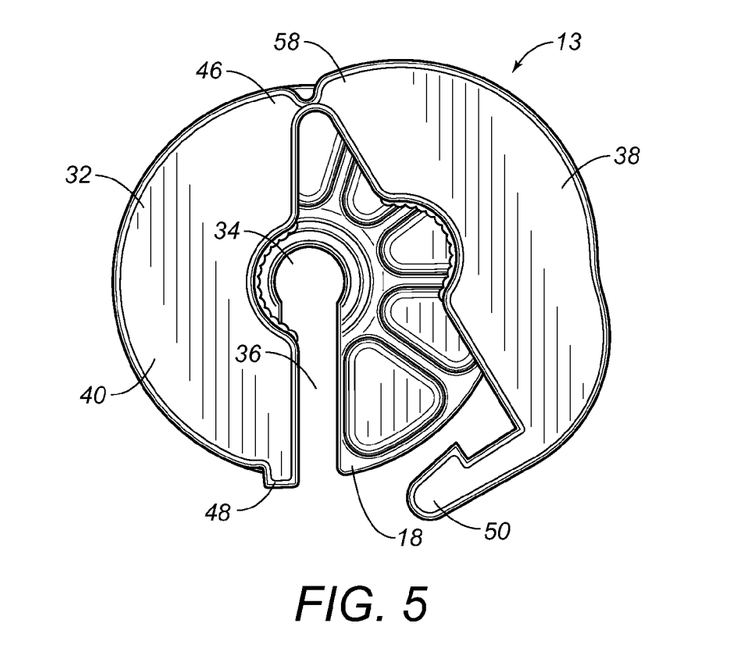
FIG. 5 shows an opposite end elevational view of the locking device of the present invention with the locking member in the unlocked position.

Referring to FIG. 5, there is shown an opposite end view of the device 13 for locking a position of a shaft 12 of a prostate immobilizer 10. The locking member 38 is in an unlocked position. End 46 of the stem portion 32 is hingedly connected to end 58 of the locking member 38. The locking member 38 can pivot with respect to the stem portion 38 so as to lock the device 13 in position on the shaft 12 of the prostate immobilizer 10.

Figure 6:
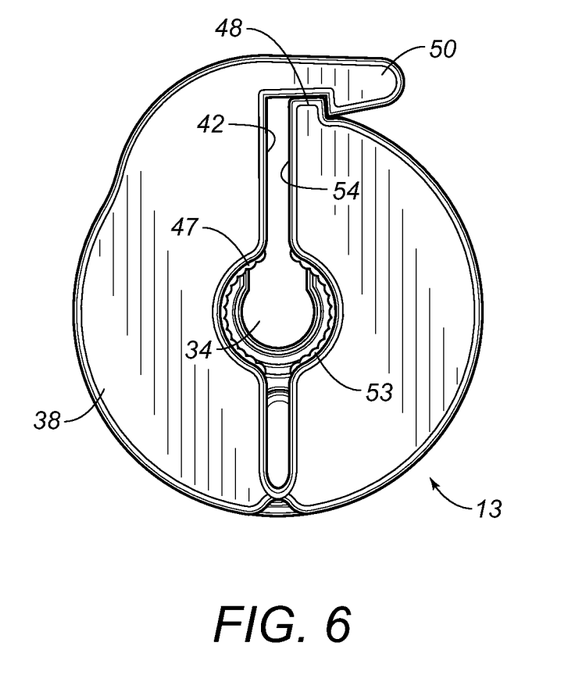
FIG. 6 shows the opposite end view of the locking device of the present invention with the locking member in a locked position.

Referring to FIG. 6, there is shown the opposite end view of the device 13 for locking a position of a shaft 12 of a prostate immobilizer 10. The locking member 38 of the device 13 is shown in the locked position. The latch 50 extends over the lip 48. The stem portion has an inner face 42 has an inner face 42. The locking member has an inner face 54. The inner face 42 is adjacent the inner face 54 when the locking member 38 is in the locked position. The curved surface 47 faces the curved area 53 so as to define the cannel 34. The ribs of the curved surface 47 and the curved area 53 compressively contact the shaft 12 so as to fix the device to the shaft 12. The position of the device 13 on the shaft 12 can be recorded by medical personnel by reading the indicia 34 on the shaft 12. The locking stopper 13 can be removed and reapplied to the shaft 12 in successive treatments of the prostate 3 so as to assure that the prostate immobilizer 10 is accurately positioned in the rectal cavity 2 adjacent the prostate 3 each time a treatment is performed. The head portion 20 and the stem portion 32 can be integrally formed of a polymeric material.

The locking stopper 13 assures that the prostate immobilizer 10 will not slide away from or be displaced from its desired position once it is applied. The locking stopper 13 is fixed so that the balloon 14 will always reside in a desired position.

The foregoing disclosure and description of the invention is illustrative and explanatory thereof. Various changes in the details of the illustrated construction can be made within the scope of the present claims without departing from the true spirit of the invention. The present invention should only be limited by the following claims and their legal equivalents.

I claim:

1. A locking device for use on a shaft of a prostate immobilizer comprising:
   a positioning member having a head portion and a stem portion, said stem portion extending from said head portion, said stem portion having a channel formed therein, said channel having a plurality of ribs formed on an inner wall thereof, said channel suitable for receiving the shaft therein; and
   a locking member connected to said stem portion, said locking member being movable between a locked position and an unlocked position, said locking member having a surface suitable for gripping the shaft when said locking member is in said locked position;
   said head portion having a generally hemispherical shape at one end thereof and a generally flat surface at the opposite end thereof, and said locking member positioned adjacent to said generally flat surface.

2. The device of claim 1, said locking member being hingedly connected to said stem portion.

3. The device of claim 2, said stem portion having a lip formed thereon, said locking member having a latch formed thereon, said latch engaging said lip when said locking member is in said locked position.

4. The device of claim 1, said channel extending through said stem portion and said head portion.

5. The device of claim 1, said plurality of ribs compressively engaging the shaft when said locking member is in said locked position.

6. The device of claim 1, said stem portion having an outer surface flush with a surface of said head portion, said locking member having an outer surface flush with another surface of said head portion when in said locked position.

7. The device of claim 1, said head portion having a longitudinal split formed therein so as to open to said channel, said longitudinal split having an opening suitable for allowing the shaft to pass therethrough and into said channel.

8. A prostate immobilizer comprising:
- a shaft having a fluid passageway extending therethrough;
- a balloon affixed over an end of said shaft such that said fluid passageway communicates with an interior of said balloon;
- a positioning member having a stem portion extending from a generally hemispherical head portion, said stem portion having a channel formed therein, said channel having a plurality of ribs formed on an inner wall thereof, said shaft received in said channel, said generally hemispherical head portion having a generally flat surface at an opposite end thereof; and
- a locking member having a locked position and an unlocked position, said locking member connected to said stem portion of said positioning member, said locking member engaging said shaft when in said locked position so as to fix said positioning member on said shaft, said plurality of ribs gripping said shaft when said locking member is in the locked position, and said locking member positioned adjacent to said generally flat surface on said generally hemispherical head portion.

9. The prostate immobilizer of claim 8, further comprising:
- a lumen extending within said shaft so as to have an end opening adjacent an end of said balloon.

10. The prostate immobilizer of claim 8, said locking member being hingedly connected to said stem portion.

11. The device of claim 8, said stem portion having a lip formed thereon, said locking member having a latch formed thereon, said latch engaging said lip when said locking member is in said locked position.

12. The prostate immobilizer of claim 8, said channel extending through said stem portion and said head portion.

13. The prostate immobilizer of claim 8, said plurality of ribs extending longitudinally through said channel.

14. The prostate immobilizer of claim 8, said stem portion having an outer surface flush with a surface of said hemispherical head portion, said locking member having an outer surface flush with another surface of said head portion when in said locked position.

15. The prostate immobilizer of claim 8, said locking member being hingedly connected to said stem portion.

16. The prostate immobilizer of claim 8, said head portion having a longitudinal split formed therein so as to open to said channel, said longitudinal split having an opening with a width greater than a diameter of said shaft.

17. The locking device of claim 1, wherein said head portion having a hemispherical shape with a longitudinal split communicating with a head channel, said longitudinal split being oriented at a ninety degree angle from said channel in said stem portion, said head channel suitable for receiving said shaft, said locking member hingedly connected to said stem portion, and said locking member having a locking member channel oriented at a ninety degree angle from said longitudinal split when in said locked position.

18. The prostate immobilizer of claim 8, wherein said head portion having a hemispherical shape with a longitudinal split communicating with a head channel, said longitudinal split being oriented at a ninety degree angle from said head channel in said head portion, said shaft received in said head channel, said locking member hingedly connected to said stem portion, and said locking member having a locking member channel oriented at a ninety degree angle from said longitudinal split when in said locked position.

19. A locking device for use on a shaft of a prostate immobilizer comprising:
- a semispherical head portion adjacent a locking portion,
- a channel extending centrally through said semispherical head portion and said locking portion and having a plurality of ribs formed on an inner wall thereof, wherein said channel located on said semispherical head is suitable for receiving said shaft,
- a longitudinal split communicating with said channel located on said semispherical head, with said longitudinal split being oriented at a ninety degree angle from said channel in said locking portion,
- said locking portion being hinged and being movable between a closed locked position and an open unlocked position, said locking portion having said channel oriented at a ninety degree angle from said longitudinal split when in said closed locked position
- said plurality of ribs gripping a shaft of a prostate immobilizer when said locking member is in said closed locked position and holding said semispherical head portion adjacent an anus of a patient when said prostate immobilizer is in use in a rectum of said patient.

* * * * *